(12) United States Patent
Chalekian et al.

(10) Patent No.: US 7,959,669 B2
(45) Date of Patent: Jun. 14, 2011

(54) BIFURCATED STENT WITH OPEN ENDED SIDE BRANCH SUPPORT

(75) Inventors: Aaron Chalekian, Minneapolis, MN (US); Joe Groff, Montrose, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 110 days.

(21) Appl. No.: 11/854,194

(22) Filed: Sep. 12, 2007

(65) Prior Publication Data

US 2009/0069881 A1    Mar. 12, 2009

(51) Int. Cl.
*A61F 2/06* (2006.01)

(52) U.S. Cl. ...................................................... 623/1.35

(58) Field of Classification Search .................. 623/1.35
See application file for complete search history.

(56) References Cited

U.S. PATENT DOCUMENTS

| | | | |
|---|---|---|---|
| 4,309,994 | A | 1/1982 | Grunwald |
| 4,769,005 | A | 9/1988 | Ginsburg et al. |
| 4,774,949 | A | 10/1988 | Fogarty |
| 4,896,670 | A | 1/1990 | Crittenden |
| 4,905,667 | A | 3/1990 | Foerster et al. |
| 4,906,244 | A | 3/1990 | Pinchuk et al. |
| 4,935,190 | A | 6/1990 | Tennerstedt |
| 4,994,071 | A | 2/1991 | MacGregor |
| 5,037,392 | A | 8/1991 | Hillstead |
| 5,053,007 | A | 10/1991 | Euteneuer |
| 5,087,246 | A | 2/1992 | Smith |
| 5,112,900 | A | 5/1992 | Buddenhagen et al. |
| 5,147,302 | A | 9/1992 | Euteneuer et al. |

(Continued)

FOREIGN PATENT DOCUMENTS

CA    2220864    7/1999

(Continued)

OTHER PUBLICATIONS

Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).

(Continued)

*Primary Examiner* — David Isabella
*Assistant Examiner* — Jacqueline Woznicki
(74) *Attorney, Agent, or Firm* — Vidas, Arrett & Steinkraus

(57) ABSTRACT

In some embodiments, a stent comprises a side branch structure defining an inner side branch cell. The inner side branch cell has a shape that is different from any other cell of the stent. The stent further comprises first and second support members, which are positioned on opposite sides of the side branch structure. The first and second support members each have a strut width that is greater than the width of a strut included in the side branch structure. The stent further comprises first and second connecting members, which are positioned on opposite ends of the side branch structure. Each connecting member is connected at one end to the first support member and is connected at the other end to the second support member. Each connecting member comprises a serpentine structure having a plurality of straight struts and turns. One or both of the connecting members includes at least one straight strut that has a length that is at least ten times its width. In some embodiments, each connecting member comprises at least four struts that have a length that is at least then times their width.

20 Claims, 8 Drawing Sheets

U.S. PATENT DOCUMENTS

| | | | |
|---|---|---|---|
| 5,163,989 A | 11/1992 | Campbell et al. | |
| 5,209,799 A | 5/1993 | Vigil | |
| 5,226,887 A | 7/1993 | Farr et al. | |
| 5,306,246 A | 4/1994 | Sahatijian et al. | |
| 5,318,587 A | 6/1994 | Davey | |
| 5,342,307 A | 8/1994 | Enteneuer et al. | |
| 5,342,387 A | 8/1994 | Summers | |
| 5,348,538 A | 9/1994 | Wang et al. | |
| 5,350,361 A | 9/1994 | Tsukashima et al. | |
| 5,358,475 A | 10/1994 | Mares et al. | |
| 5,387,235 A | 2/1995 | Chuter | |
| 5,403,340 A | 4/1995 | Wang et al. | |
| 5,447,497 A | 9/1995 | Sogard et al. | |
| 5,456,666 A | 10/1995 | Campbell et al. | |
| 5,456,712 A | 10/1995 | Maginot | |
| 5,458,572 A | 10/1995 | Campbell et al. | |
| 5,476,471 A | 12/1995 | Shifrin et al. | |
| 5,478,319 A | 12/1995 | Campbell et al. | |
| 5,487,730 A | 1/1996 | Marcadis et al. | |
| 5,523,092 A | 6/1996 | Hanson et al. | |
| 5,549,552 A | 8/1996 | Peters et al. | |
| 5,550,180 A | 8/1996 | Elsik et al. | |
| 5,556,383 A | 9/1996 | Wang et al. | |
| 5,591,228 A | 1/1997 | Edoga | |
| 5,607,444 A | 3/1997 | Lam | |
| 5,609,605 A | 3/1997 | Marshall et al. | |
| 5,609,627 A | 3/1997 | Goicoechea et al. | |
| 5,613,980 A | 3/1997 | Chauhan | |
| 5,617,878 A | 4/1997 | Taheri | |
| 5,632,762 A | 5/1997 | Myler | |
| 5,632,763 A | 5/1997 | Glastra | |
| 5,632,772 A | 5/1997 | Alcime et al. | |
| 5,636,641 A | 6/1997 | Fariabi | |
| 5,669,924 A | 9/1997 | Shaknovich | |
| 5,669,932 A | 9/1997 | Fischell et al. | |
| 5,676,697 A | 10/1997 | McDonald | |
| 5,683,450 A | 11/1997 | Goicoechea et al. | |
| 5,697,971 A | 12/1997 | Fischell et al. | |
| 5,707,348 A | 1/1998 | Krogh | |
| 5,709,713 A | 1/1998 | Evans et al. | |
| 5,718,684 A | 2/1998 | Gupta | |
| 5,718,724 A | 2/1998 | Goicechea et al. | |
| 5,720,735 A | 2/1998 | Dorros | |
| 5,746,745 A | 5/1998 | Abele et al. | |
| 5,749,825 A | 5/1998 | Fischell et al. | |
| 5,749,890 A | 5/1998 | Shaknovich | |
| 5,755,734 A | 5/1998 | Richter et al. | |
| 5,755,735 A | 5/1998 | Richter et al. | |
| 5,755,771 A | 5/1998 | Penn et al. | |
| 5,755,773 A | 5/1998 | Evans et al. | |
| 5,755,778 A | 5/1998 | Kleshinski | |
| 5,782,906 A | 7/1998 | Marshall et al. | |
| 5,800,520 A | 9/1998 | Fogarty et al. | |
| 5,810,767 A | 9/1998 | Klein | |
| 5,824,036 A | 10/1998 | Lauterjung | |
| 5,824,040 A | 10/1998 | Cox et al. | |
| 5,827,320 A | 10/1998 | Richter et al. | |
| 5,830,182 A | 11/1998 | Wang et al. | |
| 5,833,657 A | 11/1998 | Reinhardt et al. | |
| 5,843,172 A | 12/1998 | Yan | |
| 5,851,464 A | 12/1998 | Davila et al. | |
| 5,868,777 A | 2/1999 | Lam | |
| 5,882,334 A | 3/1999 | Sepetka et al. | |
| 5,891,108 A | 4/1999 | Leone et al. | |
| 5,893,887 A | 4/1999 | Jayaraman | |
| 5,906,640 A | 5/1999 | Penn et al. | |
| 5,922,020 A | 7/1999 | Klein et al. | |
| 5,922,021 A | 7/1999 | Jang | |
| 5,951,941 A | 9/1999 | Wang et al. | |
| 5,961,548 A | 10/1999 | Shmulewitz | |
| 5,972,017 A | 10/1999 | Berg et al. | |
| 5,972,027 A | 10/1999 | Johnson | |
| 6,013,054 A | 1/2000 | Jiun Yan | |
| 6,013,055 A | 1/2000 | Bampos et al. | |
| 6,013,091 A | 1/2000 | Ley et al. | |
| 6,017,324 A | 1/2000 | Tu et al. | |
| 6,017,363 A | 1/2000 | Hojeibane | |
| 6,030,414 A | 2/2000 | Taheri | |
| 6,033,380 A | 3/2000 | Butaric et al. | |
| 6,033,433 A | 3/2000 | Ehr et al. | |
| 6,033,434 A | 3/2000 | Borghi | |
| 6,033,435 A | 3/2000 | Penn et al. | |
| 6,048,361 A | 4/2000 | Von Oepen | |
| 6,056,775 A | 5/2000 | Borghi et al. | |
| 6,059,824 A | 5/2000 | Taheri | |
| 6,068,655 A | 5/2000 | Seguin et al. | |
| 6,071,285 A | 6/2000 | Lashinski et al. | |
| 6,071,305 A | 6/2000 | Brown et al. | |
| 6,086,611 A | 7/2000 | Duffy et al. | |
| 6,093,203 A | 7/2000 | Uflacker | |
| 6,096,070 A | 8/2000 | Ragheb et al. | |
| 6,096,073 A | 8/2000 | Webster et al. | |
| 6,099,497 A | 8/2000 | Adams et al. | |
| 6,113,579 A | 9/2000 | Eidenschink et al. | |
| 6,117,117 A | 9/2000 | Mauch | |
| 6,117,156 A | 9/2000 | Richter et al. | |
| 6,123,721 A | 9/2000 | Jang | |
| 6,126,652 A | 10/2000 | McLeod et al. | |
| 6,129,738 A | 10/2000 | Lashinski et al. | |
| 6,129,754 A | 10/2000 | Kanesaka et al. | |
| 6,135,982 A | 10/2000 | Campbell | |
| 6,142,973 A | 11/2000 | Carleton et al. | |
| 6,143,002 A | 11/2000 | Vietmeier | |
| 6,146,356 A | 11/2000 | Wang et al. | |
| 6,159,238 A | 12/2000 | Killion et al. | |
| 6,165,195 A | 12/2000 | Wilson et al. | |
| 6,168,621 B1 | 1/2001 | Vrba | |
| 6,171,278 B1 | 1/2001 | Wang et al. | |
| 6,183,509 B1 | 2/2001 | Dibie | |
| 6,190,404 B1 | 2/2001 | Palmaz et al. | |
| 6,203,568 B1 | 3/2001 | Lombardi et al. | |
| 6,206,915 B1 | 3/2001 | Fagan et al. | |
| 6,206,916 B1 | 3/2001 | Furst | |
| 6,210,380 B1 | 4/2001 | Mauch | |
| 6,210,429 B1 | 4/2001 | Vardi et al. | |
| 6,210,433 B1 | 4/2001 | Larre | |
| 6,210,436 B1 | 4/2001 | Weadock | |
| 6,231,598 B1 | 5/2001 | Berry et al. | |
| 6,240,616 B1 | 6/2001 | Yan | |
| 6,241,762 B1 * | 6/2001 | Shanley | 623/1.17 |
| 6,245,101 B1 * | 6/2001 | Drasler et al. | 623/1.15 |
| 6,253,443 B1 | 7/2001 | Johnson | |
| 6,254,593 B1 | 7/2001 | Wilson | |
| 6,254,632 B1 | 7/2001 | Wu et al. | |
| 6,258,115 B1 | 7/2001 | Dubrul | |
| 6,258,116 B1 | 7/2001 | Hojeibane | |
| 6,258,121 B1 | 7/2001 | Yang et al. | |
| 6,261,305 B1 | 7/2001 | Marotta et al. | |
| 6,261,316 B1 | 7/2001 | Shaolian et al. | |
| 6,261,320 B1 | 7/2001 | Tam et al. | |
| 6,264,662 B1 | 7/2001 | Lauterjung | |
| 6,264,686 B1 | 7/2001 | Rieu et al. | |
| 6,273,908 B1 | 8/2001 | Ndondo-Lay | |
| 6,273,913 B1 | 8/2001 | Wright et al. | |
| 6,280,413 B1 | 8/2001 | Clark et al. | |
| 6,287,628 B1 | 9/2001 | Hossainy et al. | |
| 6,290,673 B1 | 9/2001 | Shanley | |
| 6,293,967 B1 | 9/2001 | Shanley | |
| 6,293,968 B1 | 9/2001 | Taheri | |
| 6,325,826 B1 | 12/2001 | Vardi et al. | |
| 6,328,925 B1 | 12/2001 | Wang et al. | |
| 6,334,864 B1 | 1/2002 | Amplatz et al. | |
| 6,334,870 B1 | 1/2002 | Ehr et al. | |
| 6,346,089 B1 | 2/2002 | Dibie | |
| 6,348,065 B1 | 2/2002 | Brown et al. | |
| 6,355,060 B1 | 3/2002 | Lenker et al. | |
| 6,358,552 B1 | 3/2002 | Mandralis et al. | |
| 6,361,544 B1 | 3/2002 | Wilson et al. | |
| 6,361,555 B1 | 3/2002 | Wilson | |
| 6,379,381 B1 | 4/2002 | Hossainy et al. | |
| 6,383,213 B2 | 5/2002 | Wilson et al. | |
| 6,395,018 B1 | 5/2002 | Castaneda | |
| 6,395,326 B1 | 5/2002 | Castro et al. | |
| 6,406,457 B1 | 6/2002 | Wang et al. | |
| 6,423,091 B1 | 7/2002 | Hojeibane | |
| 6,436,104 B2 | 8/2002 | Hojeibane | |
| 6,436,134 B2 | 8/2002 | Richter et al. | |

| | | |
|---|---|---|
| 6,478,816 B1 | 11/2002 | Kveen et al. |
| 6,491,666 B1 | 12/2002 | Santini, Jr. et al. |
| 6,506,437 B1 | 1/2003 | Harish et al. |
| 6,508,836 B2 | 1/2003 | Wilson et al. |
| 6,517,558 B2 | 2/2003 | Gittings et al. |
| 6,520,988 B1 | 2/2003 | Colombo et al. |
| 6,527,762 B1 | 3/2003 | Santini, Jr. et al. |
| 6,527,799 B2 | 3/2003 | Shanley |
| 6,537,256 B2 | 3/2003 | Santini, Jr. et al. |
| 6,540,779 B2 | 4/2003 | Richter et al. |
| 6,551,351 B2 | 4/2003 | Smith et al. |
| 6,551,838 B2 | 4/2003 | Santini, Jr. et al. |
| 6,558,422 B1 | 5/2003 | Baker et al. |
| 6,562,065 B1 | 5/2003 | Shanley |
| 6,579,309 B1 | 6/2003 | Loos et al. |
| 6,579,312 B2 | 6/2003 | Wilson et al. |
| 6,582,394 B1 | 6/2003 | Reiss et al. |
| 6,596,020 B2 | 7/2003 | Vardi et al. |
| 6,599,316 B2 | 7/2003 | Vardi et al. |
| 6,638,302 B1 | 10/2003 | Curcio et al. |
| 6,645,242 B1 | 11/2003 | Quinn |
| 6,656,162 B2 | 12/2003 | Santini, Jr. et al. |
| 6,669,683 B2 | 12/2003 | Santini, Jr. et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,379 B1 | 3/2004 | Brandau et al. |
| 6,713,119 B2 | 3/2004 | Hossainy et al. |
| 6,730,064 B2 | 5/2004 | Ragheb et al. |
| 6,749,628 B1 | 6/2004 | Callol et al. |
| 6,758,859 B1 | 7/2004 | Dang et al. |
| 6,764,507 B2 | 7/2004 | Shanley et al. |
| 6,773,429 B2 | 8/2004 | Sheppard, Jr. et al. |
| 6,776,793 B2 | 8/2004 | Brown et al. |
| 6,783,543 B2 | 8/2004 | Jang |
| 6,790,228 B2 | 9/2004 | Hossainy et al. |
| 6,811,566 B1 | 11/2004 | Penn et al. |
| 6,827,250 B2 | 12/2004 | Uhland et al. |
| 6,835,203 B1 * | 12/2004 | Vardi et al. .................. 623/1.34 |
| 6,858,038 B2 | 2/2005 | Heuser |
| 6,884,258 B2 | 4/2005 | Vardi et al. |
| 6,896,699 B2 | 5/2005 | Wilson et al. |
| 6,904,658 B2 | 6/2005 | Hines |
| 6,932,837 B2 | 8/2005 | Amplatz et al. |
| 6,946,092 B1 | 9/2005 | Bertolino et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,071 B2 | 1/2006 | Kocur et al. |
| 7,018,400 B2 | 3/2006 | Lashinski et al. |
| 7,041,130 B2 | 5/2006 | Santini, Jr. et al. |
| 7,052,488 B2 | 5/2006 | Uhland |
| 7,056,323 B2 | 6/2006 | Mareiro et al. |
| 7,056,338 B2 | 6/2006 | Shanley et al. |
| 7,060,091 B2 | 6/2006 | Killion et al. |
| 7,070,616 B2 | 7/2006 | Majercak et al. |
| 7,160,321 B2 | 1/2007 | Shanley et al. |
| 7,169,175 B2 | 1/2007 | Cottone, Jr. et al. |
| 7,169,179 B2 | 1/2007 | Shanley et al. |
| 7,179,288 B2 | 2/2007 | Shanley |
| 7,179,289 B2 | 2/2007 | Shanley |
| 7,208,010 B2 | 4/2007 | Shanley et al. |
| 7,208,011 B2 | 4/2007 | Shanley et al. |
| 7,220,275 B2 * | 5/2007 | Davidson et al. ............. 623/1.35 |
| 2001/0003161 A1 | 6/2001 | Vardi et al. |
| 2001/0004706 A1 | 6/2001 | Hojeibane |
| 2001/0004707 A1 | 6/2001 | Dereume et al. |
| 2001/0012927 A1 | 8/2001 | Mauch |
| 2001/0016766 A1 | 8/2001 | Vardi et al. |
| 2001/0016767 A1 | 8/2001 | Wilson et al. |
| 2001/0016768 A1 | 8/2001 | Wilson et al. |
| 2001/0025195 A1 | 9/2001 | Shaolian et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0039448 A1 | 11/2001 | Dibie |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0035392 A1 | 3/2002 | Wilson |
| 2002/0038146 A1 | 3/2002 | Harry |
| 2002/0042650 A1 | 4/2002 | Vardi et al. |
| 2002/0052648 A1 | 5/2002 | McGuckin, Jr. et al. |
| 2002/0072790 A1 | 6/2002 | McGuckin, Jr. et al. |
| 2002/0095208 A1 | 7/2002 | Gregorich et al. |
| 2002/0111675 A1 | 8/2002 | Wilson |
| 2002/0156516 A1 | 10/2002 | Vardi et al. |
| 2002/0156517 A1 | 10/2002 | Perouse |
| 2002/0163104 A1 | 11/2002 | Motsenbocker et al. |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0009209 A1 | 1/2003 | Hojeibane |
| 2003/0028233 A1 | 2/2003 | Vardi et al. |
| 2003/0050688 A1 | 3/2003 | Fischell et al. |
| 2003/0055378 A1 | 3/2003 | Wang et al. |
| 2003/0055483 A1 | 3/2003 | Gumm |
| 2003/0074047 A1 | 4/2003 | Richter |
| 2003/0083687 A1 | 5/2003 | Pallazza |
| 2003/0093109 A1 | 5/2003 | Mauch |
| 2003/0097169 A1 | 5/2003 | Brucker |
| 2003/0105511 A1 | 6/2003 | Welsh et al. |
| 2003/0114912 A1 | 6/2003 | Sequin et al. |
| 2003/0125791 A1 | 7/2003 | Sequin et al. |
| 2003/0125802 A1 | 7/2003 | Callol et al. |
| 2003/0135259 A1 | 7/2003 | Simso |
| 2003/0163157 A1 | 8/2003 | McMorrow et al. |
| 2003/0167085 A1 | 9/2003 | Shanley |
| 2003/0181923 A1 | 9/2003 | Vardi |
| 2003/0195606 A1 | 10/2003 | Davidson et al. |
| 2003/0199970 A1 | 10/2003 | Shanley |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0059406 A1 | 3/2004 | Cully et al. |
| 2004/0068161 A1 | 4/2004 | Couvillon, Jr. |
| 2004/0073294 A1 | 4/2004 | Diaz et al. |
| 2004/0088007 A1 | 5/2004 | Eidenschink |
| 2004/0093071 A1 | 5/2004 | Jang |
| 2004/0117003 A1 | 6/2004 | Ouriel et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2004/0133268 A1 | 7/2004 | Davidson et al. |
| 2004/0138732 A1 | 7/2004 | Suhr et al. |
| 2004/0138737 A1 * | 7/2004 | Davidson et al. ............. 623/1.35 |
| 2004/0142014 A1 | 7/2004 | Livack et al. |
| 2004/0143321 A1 | 7/2004 | Livack et al. |
| 2004/0143322 A1 | 7/2004 | Livack et al. |
| 2004/0148006 A1 | 7/2004 | Davidson et al. |
| 2004/0148012 A9 | 7/2004 | Jang |
| 2004/0172121 A1 | 9/2004 | Eidenschink et al. |
| 2004/0186560 A1 | 9/2004 | Alt |
| 2004/0202692 A1 | 10/2004 | Shanley et al. |
| 2004/0204750 A1 | 10/2004 | Dinh |
| 2004/0215227 A1 | 10/2004 | McMorrow et al. |
| 2004/0220661 A1 | 11/2004 | Shanley et al. |
| 2004/0225345 A1 | 11/2004 | Fischell et al. |
| 2004/0236408 A1 | 11/2004 | Shanley |
| 2004/0249449 A1 | 12/2004 | Shanley et al. |
| 2004/0267352 A1 | 12/2004 | Davidson et al. |
| 2005/0004656 A1 | 1/2005 | Das |
| 2005/0010278 A1 | 1/2005 | Vardi et al. |
| 2005/0015108 A1 | 1/2005 | Williams et al. |
| 2005/0015135 A1 | 1/2005 | Shanley |
| 2005/0043816 A1 | 2/2005 | Datta et al. |
| 2005/0060027 A1 * | 3/2005 | Khenansho et al. ......... 623/1.35 |
| 2005/0096726 A1 | 5/2005 | Sequin et al. |

| | | |
|---|---|---|
| 2005/0102017 A1 | 5/2005 | Mattison |
| 2005/0102021 A1 | 5/2005 | Osborne |
| 2005/0102023 A1* | 5/2005 | Yadin et al. .................. 623/1.15 |
| 2005/0119731 A1 | 6/2005 | Brucker et al. |
| 2005/0125076 A1 | 6/2005 | Ginn |
| 2005/0131526 A1 | 6/2005 | Wong |
| 2005/0149161 A1 | 7/2005 | Eidenschink et al. |
| 2005/0154442 A1 | 7/2005 | Eidenschink et al. |
| 2005/0154444 A1 | 7/2005 | Quadri |
| 2005/0183259 A1 | 8/2005 | Eidenschink et al. |
| 2005/0187602 A1 | 8/2005 | Eidenschink |
| 2005/0187611 A1 | 8/2005 | Ding et al. |
| 2005/0192657 A1 | 9/2005 | Colen et al. |
| 2005/0209673 A1 | 9/2005 | Shaked |
| 2005/0222668 A1 | 10/2005 | Schaeffer et al. |
| 2005/0228483 A1 | 10/2005 | Kaplan et al. |
| 2005/0273149 A1 | 12/2005 | Tran et al. |
| 2006/0015134 A1 | 1/2006 | Trinidad |
| 2006/0034884 A1 | 2/2006 | Stenzel |
| 2006/0036315 A1 | 2/2006 | Yadin et al. |
| 2006/0041303 A1 | 2/2006 | Israel |
| 2006/0045901 A1 | 3/2006 | Weber |
| 2006/0079956 A1 | 4/2006 | Eigler et al. |
| 2006/0088654 A1 | 4/2006 | Ding et al. |
| 2006/0093643 A1 | 5/2006 | Stenzel |
| 2006/0100686 A1 | 5/2006 | Bolduc |
| 2006/0122698 A1 | 6/2006 | Spencer et al. |
| 2006/0173528 A1 | 8/2006 | Feld et al. |
| 2006/0206188 A1 | 9/2006 | Weber et al. |
| 2006/0287712 A1 | 12/2006 | Eidenschink |
| 2007/0005126 A1 | 1/2007 | Tischler |
| 2007/0050016 A1 | 3/2007 | Gregorich et al. |
| 2007/0073376 A1 | 3/2007 | Krolik et al. |
| 2007/0073384 A1 | 3/2007 | Brown et al. |
| 2007/0100434 A1 | 5/2007 | Gregorich et al. |
| 2007/0142902 A1* | 6/2007 | Yadin ............................ 623/1.16 |
| 2007/0173787 A1 | 7/2007 | Huang et al. |
| 2007/0173923 A1 | 7/2007 | Savage et al. |
| 2007/0208414 A1 | 9/2007 | Sorenson et al. |
| 2008/0119925 A1* | 5/2008 | Yadin ............................ 623/1.35 |
| 2008/0172123 A1* | 7/2008 | Yadin ............................ 623/1.35 |
| 2008/0177377 A1* | 7/2008 | Meyer et al. ................... 623/1.35 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| DE | 19921788 | 11/2000 |
| EP | 0479730 | 10/1991 |
| EP | 0565796 | 10/1993 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0950386 | 10/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 94/23787 | 10/1994 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/23228 | 6/1998 |
| WO | 98/36709 | 8/1998 |
| WO | 98/36784 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15108 | 4/1999 |
| WO | 99/15109 | 4/1999 |
| WO | 99/23977 | 5/1999 |
| WO | 99/24104 | 5/1999 |
| WO | 99/29262 | 6/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/17577 | 3/2001 |
| WO | 01/21095 | 3/2001 |
| WO | 01/21109 | 3/2001 |
| WO | 01/21244 | 3/2001 |
| WO | 01/26584 | 4/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/66036 | 9/2001 |
| WO | 01/70294 | 9/2001 |
| WO | 01/70299 | 9/2001 |
| WO | 01/74273 | 10/2001 |
| WO | 01/89409 | 11/2001 |
| WO | 01/91918 | 12/2001 |
| WO | 01/93781 | 12/2001 |
| WO | 02/00138 | 1/2002 |
| WO | 02/053066 | 7/2002 |
| WO | 02/068012 | 9/2002 |

| WO | 03/007842 |   | 1/2003 |
| --- | --- | --- | --- |
| WO | 03/055414 |   | 7/2003 |
| WO | 03/063924 |   | 8/2003 |
| WO | 2004/026174 |   | 4/2004 |
| WO | 2004/026180 |   | 4/2004 |
| WO | 2005/009295 |   | 2/2005 |
| WO | 2005/014077 | * | 2/2005 |
| WO | 2005/041810 | * | 5/2005 |
| WO | 2005/122959 | * | 12/2005 |
| WO | 2006/028925 | * | 3/2006 |
| WO | 2006/074476 | * | 7/2006 |
| WO | 2006/127127 | * | 11/2006 |
| WO | 2008/033412 | * | 3/2008 |
| WO | 2008/088420 | * | 7/2008 |

OTHER PUBLICATIONS

Katoh, M.D., Osamu, "New Double Wire Technique to Stent Ostial Lesions," Catheterization and Cardiovascular Diagnosis, vol. 40, pp. 400-402 (Apr. 1997).

Lewis, M.D. Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).

Yamashita, M.D., PhD., Takehiro, "Birfurcation Lesions: Two Stents Versus One Stent—Immediate and Follow-up Results," Journal of the American College of Cardiology, vol. 35:5, pp. 1145-1151 (Apr. 2000).

Satler, M.D., Lowell F., "Bifurcation Disease: To Treat or Not to Treat," Catheterization and Cardiovascular Interventions, vol. 50, pp. 411-412 (2000).

U.S. Appl. No. 60/844,011, filed Sep. 12, 2006; Inventor: Broome et al.*

U.S. Appl. No. 09/663,111, filed Sep. 15, 2000; Inventor: Davidson et al.

U.S. Appl. No. 09/614,472, filed Jul. 11, 2000; Inventor: Davidson et al.

U.S. Appl. No. 09/325,996, filed Jun. 4, 1999; Inventor: Vardi et al.

Chevalier, M.D., Bernard, "Placement of Coronary Stents in Bifurcation Lesions by the "Culotte" Technique," The American Journal of Cardiology, vol. 82, pp. 943-949 (Oct. 15, 1998).

Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).

Caputo, Ronald P., "Stent Jail: A Minimum-Security Prison," The American Journal of Cardiology, vol. 77, pp. 1226-1230 (Jun. 1, 1996).

Colombo, M.D., Antonio, "" Kissing" Stent for Bifurcational Coronary Lesions," Catheterization and Cardiovascular Diagnosis, vol. 30, pp. 327-330 (Dec. 1993).

* cited by examiner

BIFURCATED STENT WITH OPEN ENDED SIDE BRANCH SUPPORT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries. Even some stent designs that include a dedicated side branch structure can present difficulty in some instances, as they generally require precise placement with respect to the bifurcation.

There remains a need for novel stent designs that include a dedicated side branch structure, which allow for a greater range of initial placement orientations while still providing proper support to a bifurcation after expansion of the stent and outward deployment of the side branch support structure.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, a stent comprises a side branch structure defining an inner side branch cell. The inner side branch cell has a shape that is different from any other cell of the stent. The stent further comprises first and second support members, which are positioned on opposite sides of the side branch structure. The first and second support members each have a strut width that is greater than the width of a strut included in the side branch structure. The stent further comprises first and second connecting members, which are positioned on opposite ends of the side branch structure. Each connecting member is connected at one end to the first support member and is connected at the other end to the second support member. Each connecting member comprises a serpentine structure having a plurality of straight struts and turns. One or both of the connecting members includes at least one straight strut that has a length that is at least ten times its width. In some embodiments, each connecting member comprises at least four struts that have a length that is at least ten times their width.

In some embodiments, a stent comprises a side branch structure defining an inner side branch cell. The inner side branch cell has a shape that is different from any other cell of the stent. The stent further comprises a discontinuous support ring that is positioned around the side branch structure, which comprises a first support member, a second support member, a proximal support member and a distal support member. Each support member has a strut width that is greater than the width of a strut included in the side branch structure. The first and second support members are positioned on opposite sides of the side branch structure. The proximal and distal support members are positioned on opposite ends of the side branch structure. The stent further comprises a plurality of partial serpentine bands. Each partial serpentine band extends around a portion of the stent circumference. Each partial serpentine band is connected at one end to the first support member and is connected at the other end to the second support member. The stent further comprises a plurality of full serpentine bands, each full serpentine band extending around a full circumference of the stent. The proximal support member is not directly connected to any partial serpentine band and the distal support member is not directly connected to any partial serpentine band.

In some embodiments, a stent comprises a side branch structure defining an inner side branch cell. The inner side branch cell has a shape that is different from any other cell of the stent. The stent further comprises first and second support members, which are positioned on opposite sides of the side branch structure. The first and second support members each have a strut width that is greater than the width of a strut included in the side branch structure. The stent further comprises a plurality of full serpentine bands including a first full serpentine band and a second full serpentine band. Each full serpentine band extends around a full circumference of the stent. The first full serpentine band comprises a first portion and a second portion, wherein struts of the first portion are shorter than struts of the second portion. The second full serpentine band comprises a first portion and a second portion, wherein struts of the first portion are shorter than struts of the second portion. The first portion of the first full serpentine band and the first portion of the second full serpentine band are oriented on opposite ends of the side branch structure.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
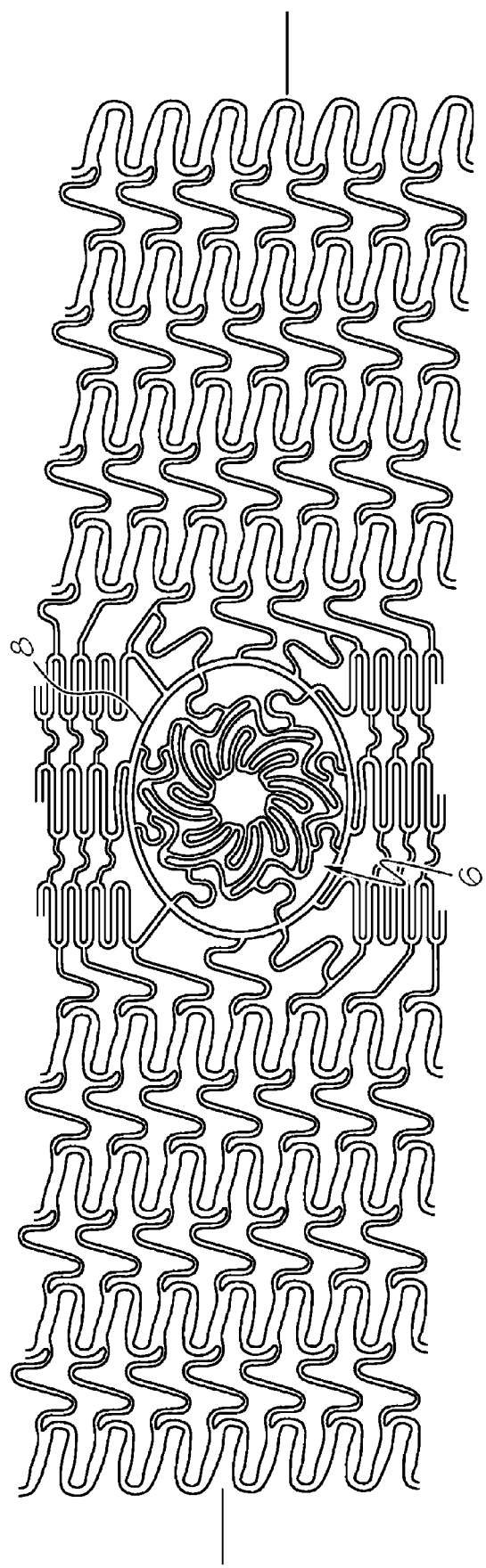
FIG. 1 shows a flat pattern for a Prior Art stent design.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The entire disclosures of U.S. Patent Application Nos. 60/844,011, 60/859,460, 11/752,837, 11/653,589 and 11/706,082, and U.S. Pat. No. 7,220,275 are hereby incorporated herein by reference in their entireties.

FIG. 1 shows an example of a Prior Art stent design that includes a prior art side branch structure 6 designed to expand into and support a vessel bifurcation. The stent also includes a prior art support ring 8, which fully encircles and provides support to the prior art side branch structure 6. Although designs having a fully encircling prior art support ring 8 provide good vessel support to the bifurcation, such stents require precise placement with respect to the bifurcation. The prior art support ring 8 should be placed longitudinally and rotationally centered under the bifurcation. When delivering a stent to a bodily vessel under fluoroscopy, such precise placement can be difficult.

The inventive stents described herein provide support members that support the side branch structure without completely encircling the side branch structure. The inventive stent patterns allow for greater longitudinal and rotational freedom in placement of the stent because the inventive support structures allow the side branch structure a greater freedom of movement in both longitudinal and circumferential directions.

Figure 2:
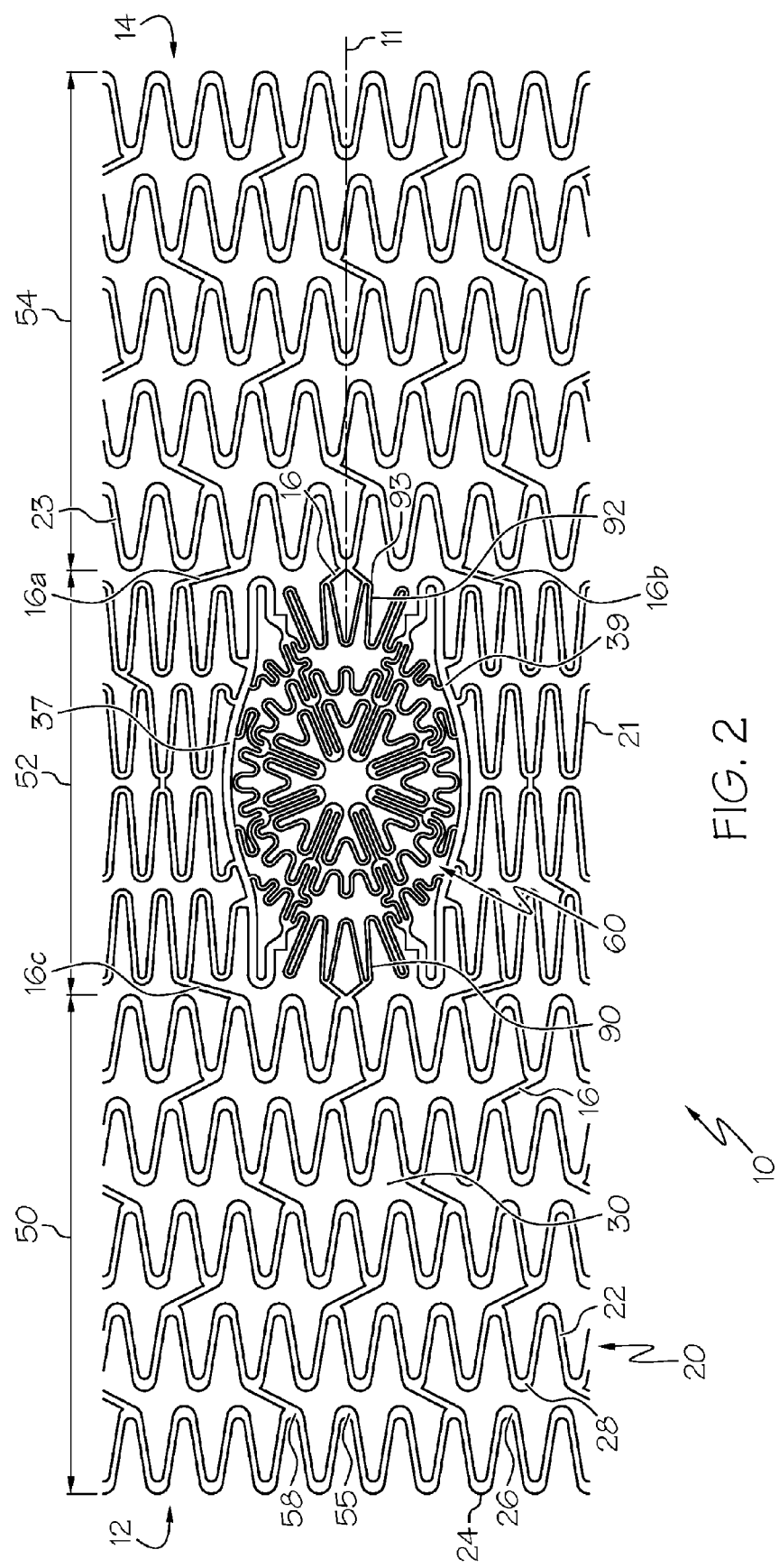
FIG. 2 shows a flat pattern for an embodiment of a stent.

FIG. 2 shows a flat pattern for an embodiment of a stent 10 having a proximal end 12, a distal end 14 and a plurality of serpentine bands 20. Each serpentine band 20 comprises a plurality of struts 22. Circumferentially adjacent struts 22 within a serpentine band 20 are connected by turns 28. Turns 28 that point toward the proximal end 12 of the stent 10 comprise proximal peaks 24, and turns 28 that point toward the distal end 14 of the stent 10 comprise distal valleys 26. Each serpentine band 20 extends around at least a portion of the circumference of the stent 10.

In some embodiments, serpentine bands 20 that are adjacent to one another along the length of the stent 10 are connected by at least one connector strut 16. In some embodiments, a connector strut 16 spans between turns 28 of adjacent serpentine bands 20. For example, one end of a connector strut 16 can connect to a distal valley 26 of one serpentine band 20, and the other end of the connector strut 16 can connect to a proximal peak 24 of an adjacent serpentine band 20. Connector struts 16 can connect to any portion of a serpentine band 20, such as a turn 28, or in some embodiments, a strut 22.

Turns 28 can comprise connected turns 58 or unconnected turns 55 depending upon whether the turn 28 connects to a connector strut 16. A serpentine band 20 can have more unconnected turns 55 than connected turns 58. In some embodiments, a serpentine band 20 has three unconnected turns 55 for each connected turn 58. The 3:1 ratio of unconnected turns 55 to connected turns 58 can also apply to the proximal peaks 24 and to the distal valleys 26.

A stent 10 further comprises a plurality of cells 30. A cell 30 comprises an opening in the stent 10 between the structural framework elements, such as serpentine bands 20 and connector struts 16. In some embodiments, a cell 30 may be bounded by a serpentine band 20, a connector strut 16, another serpentine band 20 and another connector strut 16.

In some embodiments, a stent 10 comprises a first end region 50, a central region 52 and a second end region 54. Each region 50, 52, 54 extends across a portion of the length of the stent 10. Each region 50, 52, 54 includes a plurality structural framework elements, for example a plurality of serpentine bands 20. In some embodiments, all of the serpentine bands 20 within a given region 50, 52, 54 are similar in size and shape. In some embodiments, various serpentine bands 20 within a given region 50, 52, 54 can be different in size, shape, strut width, wavelength λ, etc.

In some embodiments, the central region 52 further comprises a side branch structure 60, a first support member 37 and a second support member 39. In various embodiments, some or all of the serpentine bands 20 located in the central region 52 extend about a portion of the stent circumference, and therefore can comprise partial serpentine bands 21. In some embodiments, a partial serpentine band 21 is connected at one end to the first support member 37 and is connected at the other end to the second support member 39.

Figure 2A:
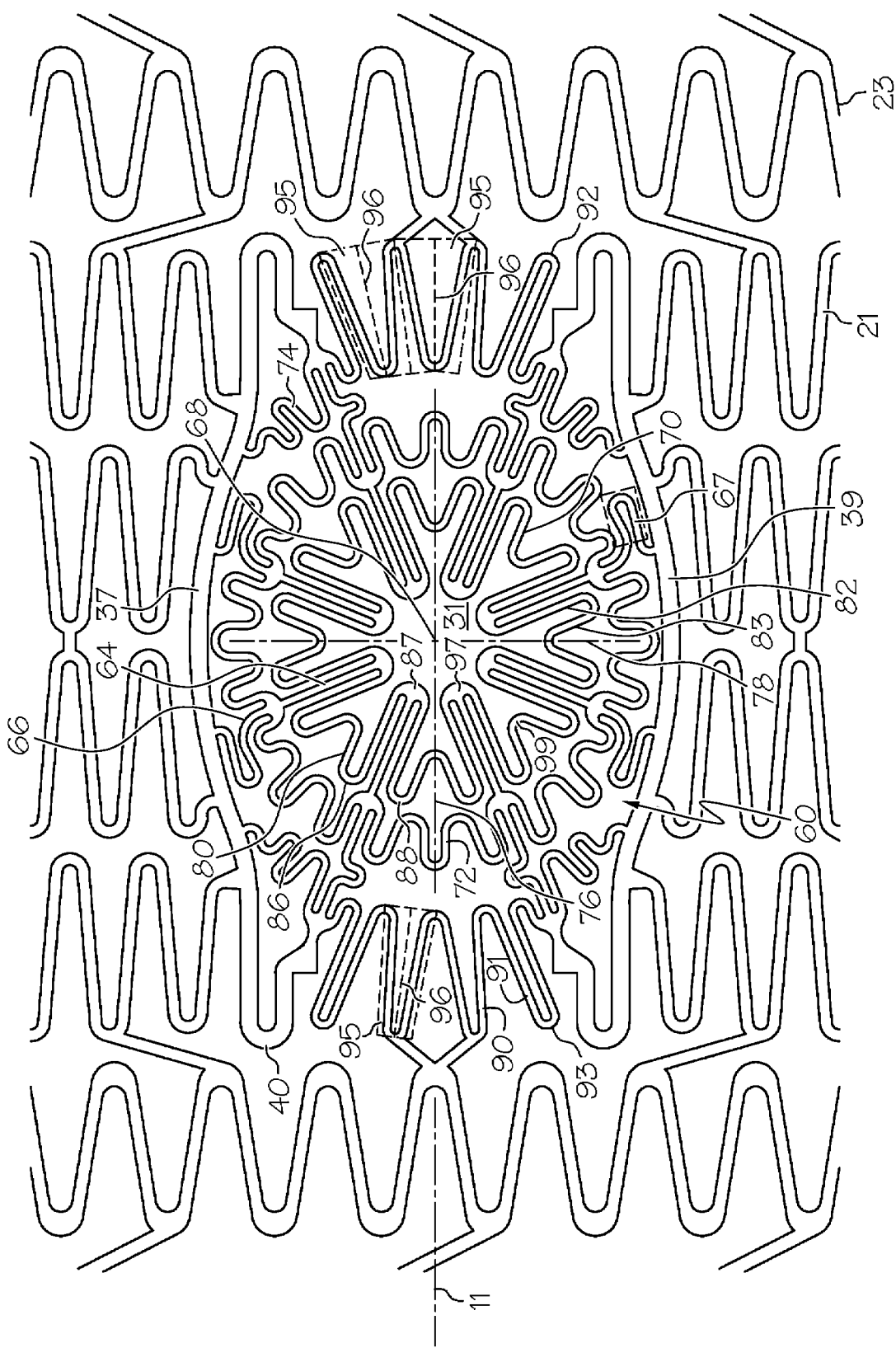
FIG. 2A shows a portion of FIG. 2 in greater detail.

FIG. 2A shows a portion of FIG. 2 in greater detail, such as the side branch structure 60.

The side branch structure 60 comprises structural elements that can displace outwardly from other portions of the stent 10, for example extending into a side branch vessel. In various embodiments, the specific configuration of the side branch structure 60 can be any side branch configurations disclosed in any of the patent applications and patents that are incorporated herein by reference.

In some embodiments, the side branch structure 60 comprises an inner or first serpentine ring 70 that extends around and defines an inner side branch cell 31. The inner side branch cell 31 can be shaped differently from all other cells 30 of the stent 10. A side branch center point 68 comprises the center of the inner side branch cell 31. In some embodiments, the first serpentine ring 70 is centered upon the side branch center point 68. The side branch center point 68 further comprises an intersection between a side branch major axis 76, which spans in a stent longitudinal direction, and a side branch minor axis 78, which spans in a stent circumferential direction. In some embodiments, the side branch major axis 76 is parallel to a stent longitudinal axis 11.

In some embodiments, the first serpentine ring 70 comprises a plurality of alternating struts 80 and turns 86. In some embodiments, each strut 80 is straight along its length. In some embodiments, each strut 80 of the first serpentine ring 70 has the same length.

In some embodiments, the struts 80 of the first serpentine ring 70 comprise first inner struts 82 and second inner struts 83. The first inner struts 82 are longer than the second inner struts 83. In some embodiments, each first inner strut 82 has the same length, and each second inner strut 83 has the same length. In some embodiments, the struts 80 of the first serpentine ring 70 are arranged in a repeating pattern of two adjacent first inner struts 82 and then two adjacent second inner struts 83. The repeating pattern is encountered as the first serpentine ring 70 is traversed around its periphery.

In some embodiments, the turns 86 of the first serpentine ring 70 comprise alternating inner turns 87 and outer turns 88. Turns 86 that point inward with respect to the side branch, for example pointing toward the side branch center point 68, comprise inner turns 87. Turns 86 that point outward with respect to the side branch, for example pointing away from the side branch center point 68, comprise outer turns 88. In some embodiments, the inner turns 87 further comprise alternating first inner turns 97 and second inner turns 99. Thus, the inner turns 87 located on either side of a first inner turn 97 comprise second inner turns 99, and the inner turns 87 located on either side of a second inner turn 99 comprise first inner turns 97. The first inner turns 97 are located closer to the side branch center point 68 than the second inner turns 99.

In some embodiments, the first inner turns 97 are each located an equal distance away from the side branch center point 68, and thus can be considered aligned around a first reference circle (not illustrated) that is centered upon the side branch center point 68. In some embodiments, the first inner turns 97 are also equally distributed around the circumference of the first reference circle.

In some embodiments, the second inner turns 99 are each located an equal distance away from the side branch center point 68, and thus can be considered aligned around a second reference circle (not illustrated) that is centered upon the side branch center point 68. In some embodiments, the second inner turns 99 are equally distributed around the circumference of the second reference circle.

In some embodiments, each first inner strut 82 is connected at an inner end to a first inner turn 97 and is connected at an outer end to an outer turn 88. Each second inner strut 83 is connected at an inner end to a second inner turn 99 and is connected at an outer end to an outer turn 88.

In some embodiments, the outer turns 88 are each located an equal distance away from the side branch center point 68, and thus can be considered aligned around a third reference circle (not illustrated) that is centered upon the side branch center point 68.

In some embodiments, the first serpentine ring 70 can be symmetrical across both the side branch major axis 76 and the side branch minor axis 78.

In some embodiments, the side branch structure 60 further comprises a second serpentine ring 72 that extends around the first serpentine ring 70. In some embodiments, the second serpentine ring 72 is coaxial with the first serpentine ring 70, and thus can be centered upon the side branch center point 68.

In some embodiments, the second serpentine ring 72 comprises a plurality of alternating struts 80 and turns 86. In some embodiments, each strut 80 is straight along its length. In some embodiments, the second serpentine ring 72 can be symmetrical across both the side branch major axis 76 and the side branch minor axis 78.

In some embodiments, the side branch structure 60 further comprises a plurality of inner connectors 64. Each inner connector 64 connects between the first serpentine ring 70 and the second serpentine ring 72. In some embodiments, an inner connector 64 is connected at an inner end to a turn 86 of the first side branch ring 70 and is connected at an outer end to a turn 86 of the second side branch ring 72. In some embodiments, an inner connector 64 spans between a first inner turn 97 of the first serpentine ring 70 and a turn 86 of the second serpentine ring 72. In some embodiments, an inner connector extends in a side branch radial direction and thus extends parallel to a radial line that passes through the side branch center point 68. In some embodiments, the number of inner connectors 64 is equal to the number of first inner turns 97 of the first serpentine ring 70.

In some embodiments, the side branch structure 60 further comprises a plurality of outer connectors 66. Each outer connector 66 connects between a portion of the side branch structure 60 and another portion of the stent, such as a support member 37, 39. In some embodiments, each outer connector 66 is connected at one end to a turn 86 of the second serpentine ring 72 and is connected at the other end to a support member 37, 39. In some embodiments, an outer connector 66 comprises a loop 67, wherein the outer connector 66 connects at one location to a support member 37, 39, extends in a first direction, loops back in a direction substantially opposite the first direction, and then connects to the side branch structure 60. The loop 67 provides the outer connector 66 with a strut length that allows the side branch structure 60 to displace outwardly, for example radially outward from the stent, and/or laterally, such as in a stent longitudinal or circumferential direction, during expansion of the side branch structure 60.

The first support member 37 and the second support member 39 are positioned on opposite sides of the side branch structure 60. Thus, the first support member 37 is circumferentially adjacent to the side branch structure 60 in one circumferential direction, while the second support member is circumferentially adjacent to the side branch structure 60 in an opposite circumferential direction.

In some embodiments, the first support member 37 comprises a mirror image of the second support member 39, wherein the mirror image is taken across the side branch major axis 76. In some embodiments, each support member 37, 39 defines a first portion that comprises a mirror image of a second portion, wherein the mirror image is taken across the side branch minor axis 78.

In some embodiments, each support member 37, 39 comprises straight portions and portions having curvature, for example being concave with respect to the side branch center point 68. In some embodiments, each support member 37, 39 comprises multiple straight portions that are parallel, for example extending parallel to the side branch major axis 76. In some embodiments, parallel straight portions can be connected by a turn 40, for example a turn 40 that extends 180 degrees.

In some embodiments, each support member 37, 39 comprises a strut width that is greater than the width of a strut 80 of the side branch structure 60. In some embodiments, each support member 37, 39 comprises a strut width that is at least twice as much as the width of a strut 80 of the side branch structure 60. In some embodiments, each support member 37, 39 comprises a strut width that is greater than the width of any strut 80 of the side branch structure 60. In some embodiments, a support member 37, 39 comprises a constant strut width.

In some embodiments, the stent 10 further comprises a first connecting member 90 and a second connecting member 92. In some embodiments, the first connecting member 90 and the second connecting member 92 are located on opposite ends of the side branch structure 60. Thus, the first connecting member 90 can be located proximal to the side branch structure 60 and the second connecting member 92 can be located distal to the side branch structure 60.

Each connecting member 90, 92 comprises a serpentine structure having a plurality of struts 91 and turns 93. Each connecting member strut 91 can be straight along its length. In some embodiments, each connecting member 90, 92 comprises at least eight struts 91 and nine turns 93. In some embodiments, each connecting member 90, 92 comprises at least one strut 91 wherein a length of the strut is at least ten times its width. In some embodiments, each connecting member 90, 92 comprises at least four of such struts. In some embodiments, each connecting member 90, 92 comprises at least eight of such struts. In some embodiments, each connecting member 90, 92 comprises at least one strut 91 that is longer than any strut 80 of the first serpentine ring 70. In some embodiments, each connecting member 90, 92 comprises a plurality of struts 91 that are longer than any strut 80 of the first serpentine ring 70.

In some embodiments, the struts 91 of each connecting member 90, 92 comprise a width equal to the width of a strut 80 of the first serpentine ring 70.

In some embodiments, the struts 91 of each connecting member 90, 92 define at least one ancillary petal structure 95 comprising a pair of struts 91 that are adjacent one another. In some embodiments, an axis 96 of an ancillary petal 95 is oriented in a side branch radial direction and will extend through the side branch center point 68. In some embodiments, the each connecting member 90, 92 defines a plurality of ancillary petals 95. In some embodiments, the each connecting member 90, 92 defines at least three ancillary petals 95.

In some embodiments, the first connecting member 90 comprises a mirror image of the second connecting member 92, wherein the mirror image is taken across the side branch minor axis 78. In some embodiments, each connecting member 90, 92 comprises a first portion and a second portion, wherein the first portion is a mirror image of the second portion taken across the side branch major axis 76.

In some embodiments, a connecting member 90, 92 is connected at one end to the first support member 37 and is connected at the other end to the second support member 39.

In some embodiments, a stent 10 further comprises a plurality of joining members 74. Each joining member 74 comprises a serpentine structure that connects to a support member 37, 39 at multiple locations. For example, a joining strut 74 can connect at one end to the first support member 37 and can connect at the other end to another portion of the first support member 37.

Referring again to FIG. 2, in some embodiments, a connector 16a can connect between a partial serpentine band 21 and a full serpentine band 23. Desirably, the connector 16a is oriented at a high angle with respect to the stent longitudinal axis 11 when the stent is viewed as a flat pattern, for example 45 degrees or more. In some embodiments, the connector 16a can be oriented in a near circumferential direction. In some embodiments, another connector 16b can connect between the partial serpentine band 21 and the full serpentine band 23. In some embodiments, one connector 16a can comprise a mirror image of another connector 16b taken across the stent longitudinal axis 11, or the side branch major axis 76 (see FIG. 2A). In some embodiments, another connector 16c can comprise a mirror image of the connector 16a taken across the side branch minor axis 78 (see FIG. 2A).

In some embodiments, a connecting member 90, 92 can be connected to a full serpentine band 23 by at least one connector 16. In some embodiments, a connector 16 can span between a turn 93 of a connecting member 90, 92 and a turn 28 of a full serpentine band 23. In some embodiments, two connectors 16 can span between a connecting member 90, 92 and a full serpentine band 23, wherein each connector 16 connects to a separate turn 93 of the connecting member 90, 92, and both connectors 16 connect to the same turn 28 of the full serpentine band 23.

Figure 3:
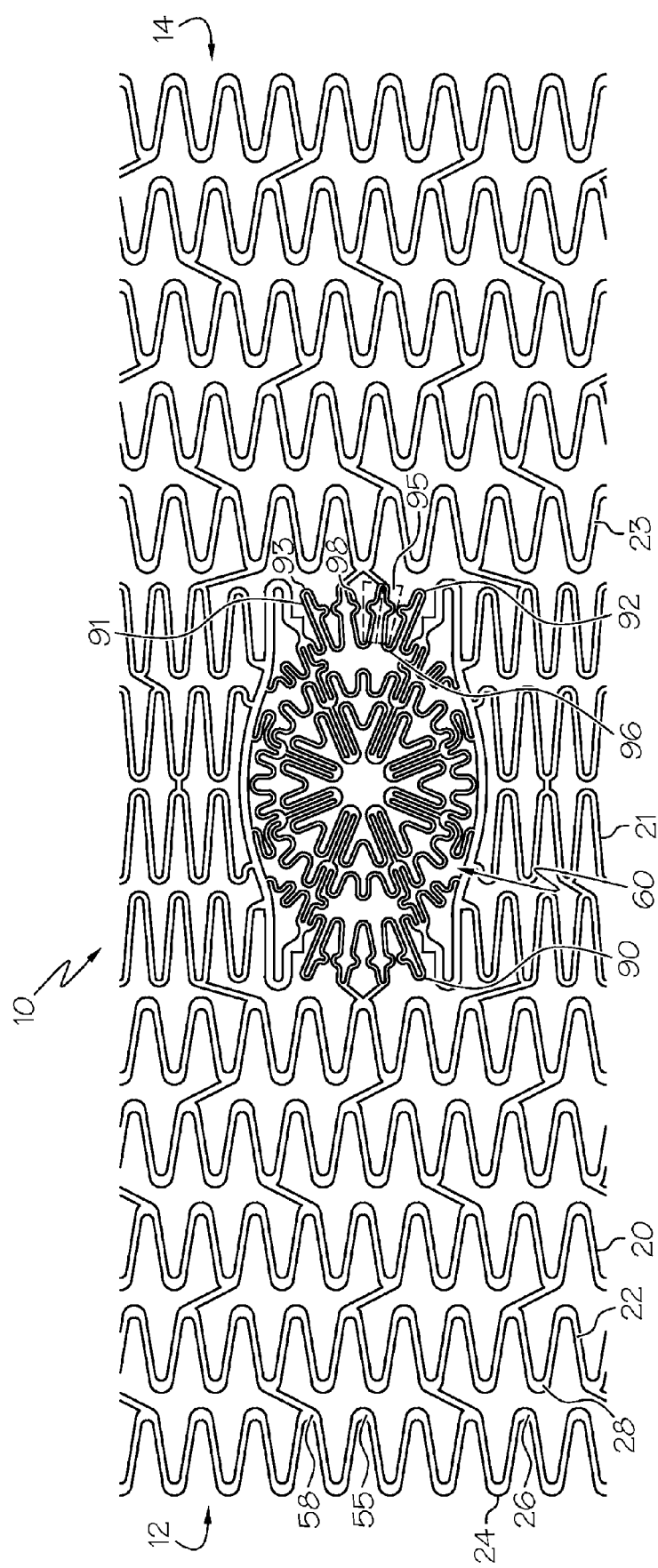
FIG. 3 shows a flat pattern for another embodiment of a stent.

FIG. 3 shows a flat pattern for another embodiment of a stent 10. The pattern has many features described with respect to FIGS. 2 and 2A.

In some embodiments, a connecting member 90, 92 can include one or more jog 98 portions. In some embodiments, a jog 98 can be considered a portion of a strut 91. A jog 98 can be similar to a turn 93. In some embodiments, a jog 98 connects between straight struts 91 that are collinear, whereas a turn 93 connects between straight struts 91 that are not collinear.

In some embodiments, two struts 91 can define an ancillary petal 95, and the two struts 91 can comprise mirror images of one another taken across an ancillary petal axis 96. In some embodiments, each strut 91 can include or connect to a jog 98, and the two jog 98 portions can comprise mirror images of one another taken across the ancillary petal axis 96.

Figure 4:
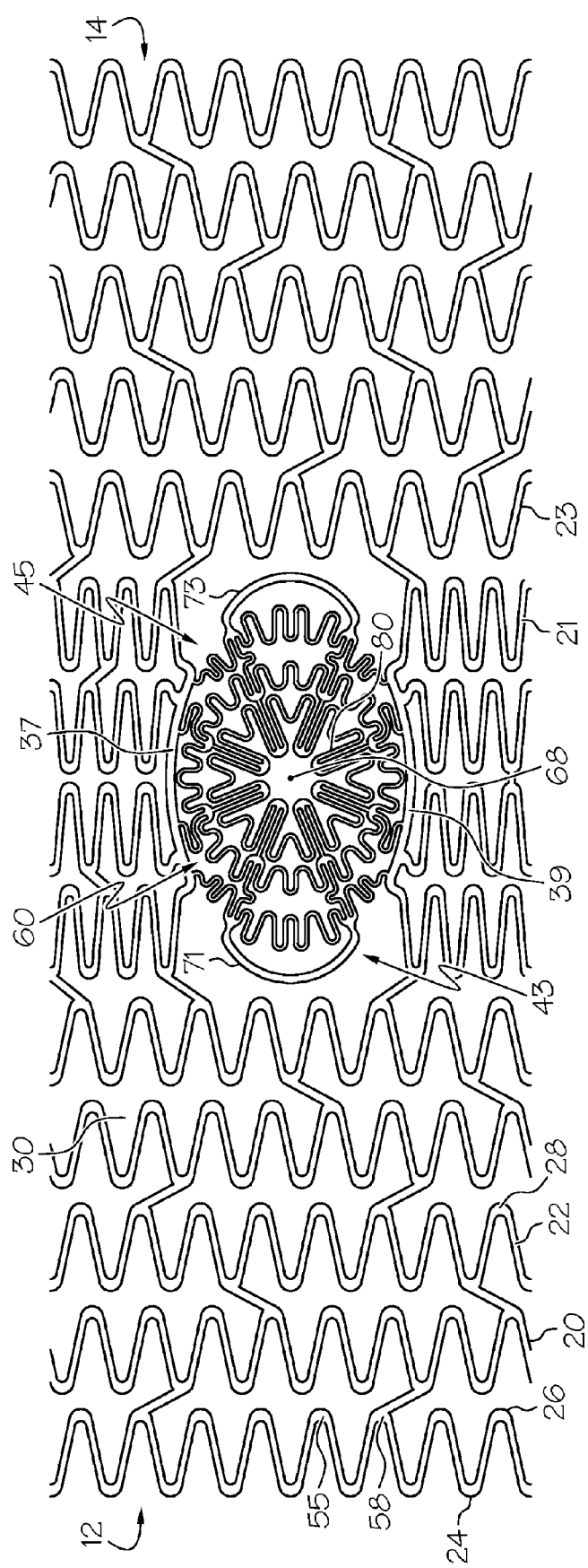
FIG. 4 shows a flat pattern for another embodiment of a stent.

FIG. 4 shows a flat pattern for another embodiment of a stent 10. Similar reference characters indicate similar features as described with respect to other Figures herein.

In some embodiments, the stent 10 comprises a discontinuous support ring 43. As used herein, the term "discontinuous support ring" is intended to mean a plurality of support members 37, 39, 71, 73 that collectively resemble a support ring that fully encircles the side branch structure, however, the discontinuous support ring 43 comprises at least one gap 45. Thus, in some embodiments, each support member 37, 39, 71, 73 can be similar to a portion of a prior art continuous support ring 8, an example of which is shown in FIG. 1. In some embodiments, a discontinuous support ring 43 can be similar to a prior art continuous support ring 8 that has had one or more portions of its structure removed to form gaps 45. In some embodiments, each support member 37, 39, 71, 73 of the discontinuous support ring 43 has the same strut width.

In various embodiments, a discontinuous support ring 43 can comprise any suitable number of support members (e.g. 37, 39), and each support member can have any suitable shape. In some embodiments, the number of gaps 45 can be equal to the number of support members (e.g. 37, 39).

In some embodiments, a discontinuous support ring 43 consists of a plurality of support members (e.g. 37, 39), wherein each support member is concave with respect to the side branch center point 68. In some embodiments, each support member (e.g. 37) comprises a mirror image of another support member (e.g. 39), wherein the mirror image is taken across an axis that intersects the side branch center point 68, for example the side branch major axis 76 or the side branch minor axis 78 (see FIG. 4A).

In some embodiments, the discontinuous support ring 43 can comprise a first support member 37 and a second support member 39. Features of the first and second support members 37, 39 can be similar to features described with respect to FIGS. 2 and 2A. In some embodiments, each support member 37, 39 is concave with respect to the side branch center point 68.

In some embodiments, the discontinuous support ring 43 further comprises a proximal support member 71 and a distal support member 73. The proximal support member 71 and the distal support member 73 are located on opposite ends of the side branch structure 60.

In some embodiments, each support member 71, 73 comprises a strut width that is greater than the width of a strut 80 of the side branch structure 60. In some embodiments, each support member 71, 73 comprises a strut width that is at least twice as much as the width of a strut 80 of the side branch structure 60. In some embodiments, each support member 71, 73 comprises a strut width that is greater than the width of any strut 80 of the side branch structure 60. In some embodiments, a support member 71, 73 comprises a constant strut width.

Figure 4A:
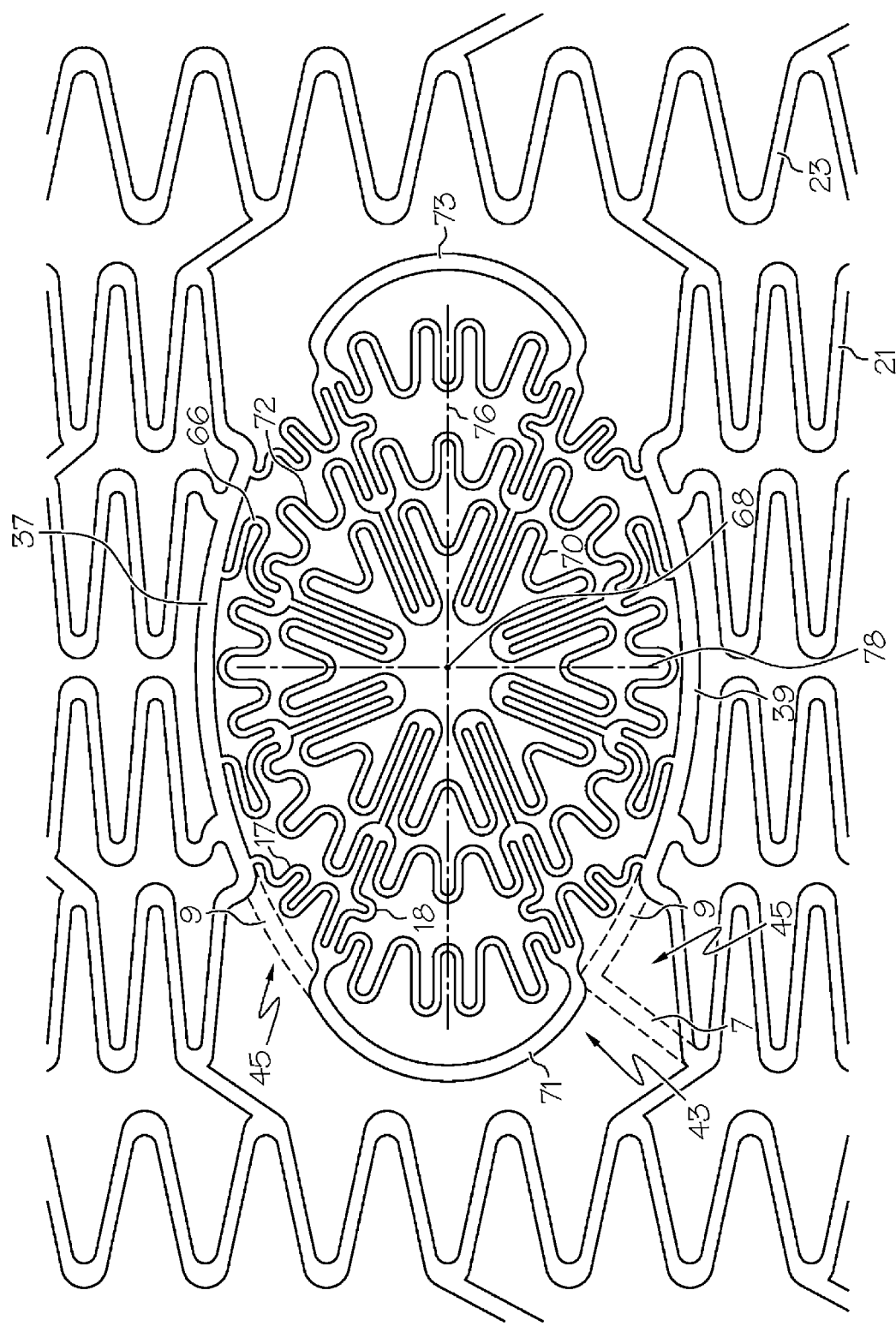
FIG. 4A shows a portion of FIG. 4 in greater detail.

FIG. 4A shows a portion of FIG. 4 is greater detail.

In some embodiments, each support member 71, 73 is concave with respect to the side branch center point 68. In some embodiments, the proximal support member 71 comprises a mirror image of the distal support member 73, wherein the mirror image is taken across the side branch minor axis 78. In some embodiments, each support member 71, 73 comprises a first portion and a second portion, wherein the first portion is a mirror image of the second portion taken across the side branch major axis 76.

The discontinuous support ring 43 defines a perimeter around the side branch structure 60 but does not form a closed, continuous ring. For example, in places where a prior art support ring included structure 9, the discontinuous support ring 43 comprises a gap 45. In some embodiments, a discontinuous support ring 43 comprises a plurality of gaps 45, such as at least two, at least four, or at least six or more gaps 45.

In some embodiments, the proximal and distal support members 71, 73 are not directly supported by any serpentine band 20 structure. For example, in some embodiments, a support member 71, 73 is only connected to joining stent structure 18 that connects to the side branch structure 60 and/or connects to another portion of the discontinuous support ring 43, such as the first or second support members 37, 39. Thus, in some embodiments, the proximal and distal support members 71, 73 are only connected to serpentine band 20 structure via the first or second support members 37, 39. Whereas a prior art support ring may have been connected to a serpentine band 20 by a connection 7, the inventive stent includes a gap 45. In some embodiments, the proximal and distal support members 71, 73 are not directly connected to any partial serpentine band 21.

In some embodiments, the stent 10 comprises a plurality of serpentine joining members 17, each joining member spanning between two members 37, 39, 71, 73 of the discontinuous support ring 43. Each serpentine joining member 17 comprises a length that is greater than the distance across a gap 45 between the two members 37, 39, 71, 73 of the discontinuous support ring 43 that the joining member 17 spans between. Thus, the members 37, 39, 71, 73 of the discontinuous support ring 43 remain indirectly connected by a structure 17 that allows a greater freedom of movement in any direction than a prior art continuous support ring.

Figure 5:
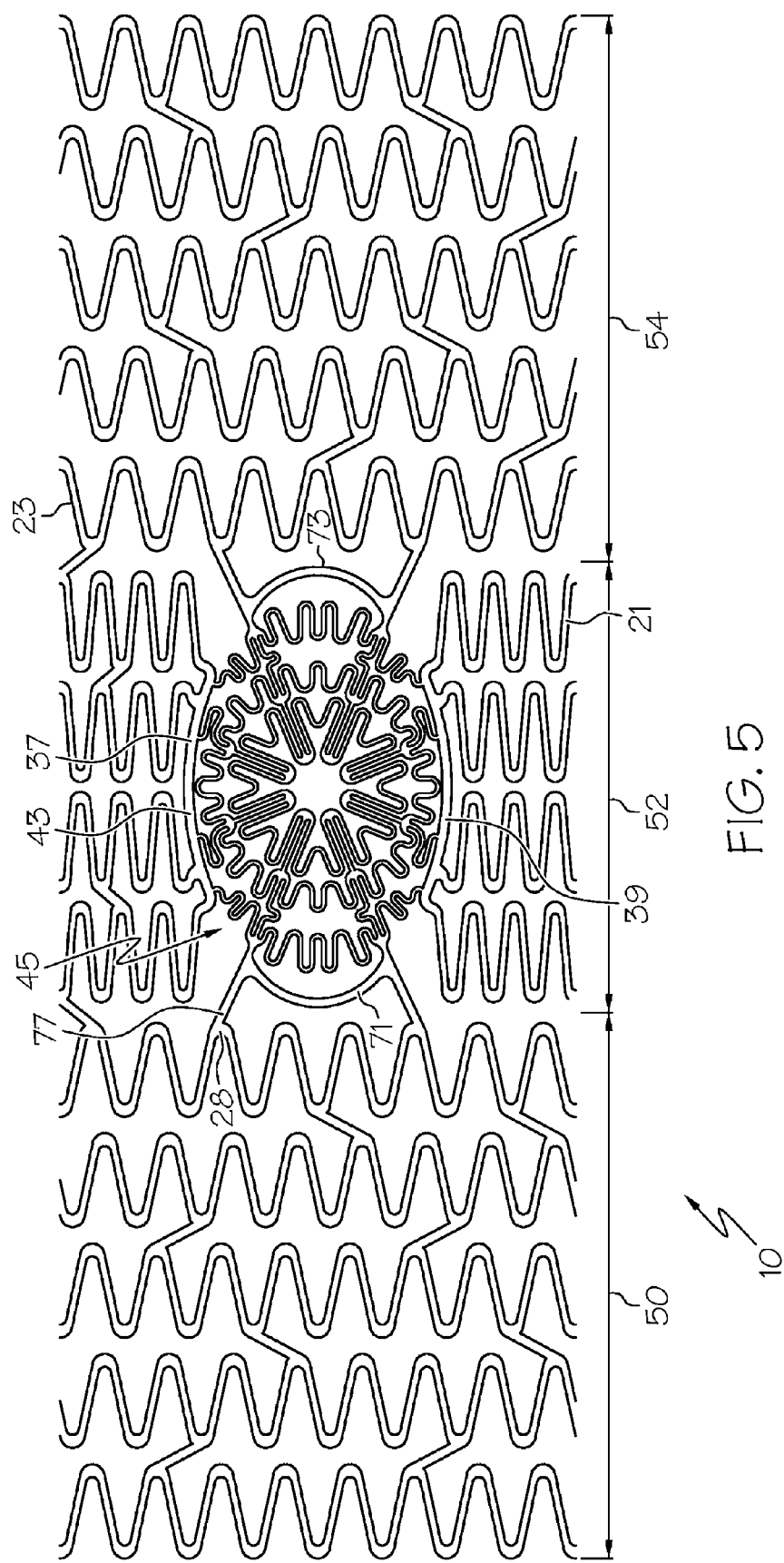
FIG. 5 shows a flat pattern for another embodiment of a stent.

FIG. 5 shows a flat pattern for another embodiment of a stent 10. The pattern has many features described with respect to FIGS. 4 and 4A, for example as indicated by like reference numerals.

In some embodiments, the proximal support member 71 and/or the distal support member 73 can comprise a strut portion 77 that connects to a portion of the stent 10 outside of the central region 52, for example connecting to a portion of the stent in the first end region 50 or second end region 54. In some embodiments, a strut portion 77 can connect between a concave portion of the support member 71, 73 and a full serpentine band 23. In some embodiments, a strut portion 77 can connect to a turn 28 of a full serpentine band 23.

In some embodiments, a proximal and/or distal support member 71, 73 can comprise two strut portions 77 that connect to a portion of the stent 10 outside of the central region 52. In some embodiments, both strut portions 77 can connect to the same full serpentine band 23. In some embodiments, a support member 71, 73 comprises a first strut portion 77 that connects to a first turn 28 of a full serpentine band 23, and comprises a second strut portion 77 that connects to a second turn 28 of the full serpentine band 23.

Figure 6:
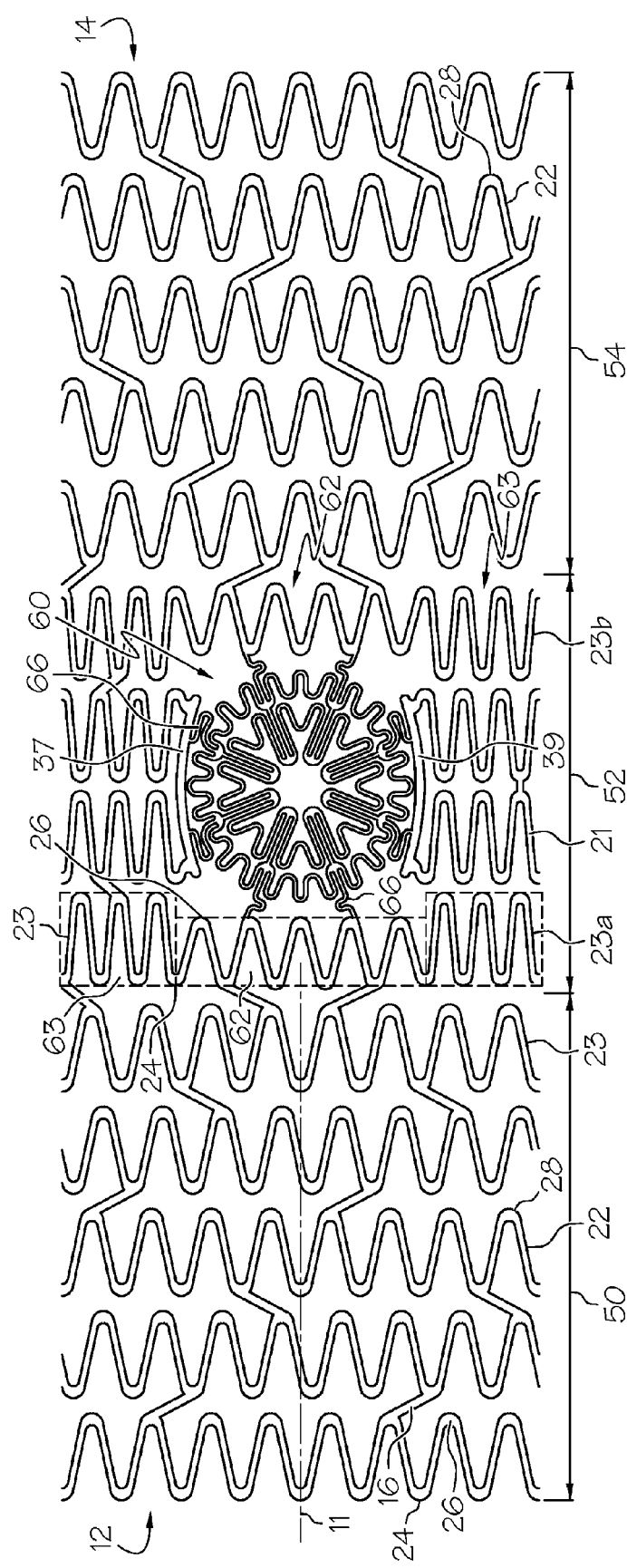
FIG. 6 shows a flat pattern for another embodiment of a stent.

FIG. 6 shows a flat pattern for another embodiment of a stent 10. The pattern has many features described with respect to FIGS. 4 and 4A, for example as indicated by like reference numerals.

In some embodiments, the central region 52 comprises one or more partial serpentine bands 21 and one or more full serpentine bands 23. In some embodiments, each partial serpentine band 21 connects between the first support member 37 and the second support member 39.

In some embodiments, a full serpentine band 23 comprises a first portion 62 and a second portion 63, wherein the first portion 62 comprises struts 22 that are shorter than the struts 22 of the second portion 63. In some embodiments, the second portion 63 spans a greater distance along the stent longitudinal axis 11 than the first portion 62. In various embodiments, a first portion 62 can comprise at least four struts 22, at least six struts 22, or at least eight or more struts 22. In some embodiments, the struts 22 of the first portion 62 account for less than one-half of the total number of struts 22 included in the full serpentine band 23.

In some embodiments, the first portion 62 spans around a portion of the circumference of the stent 10, while the second portion 63 occupies the balance of the circumference. In some embodiments, the first portion 62 is aligned with the side branch structure 60 in a stent longitudinal direction, while the second portion 63 is aligned with one or more partial serpentine bands 21.

In some embodiments, the central region 52 comprises a first full serpentine band 23a and a second full serpentine band 23b. The first and second full serpentine bands 23a, 23b can be located on opposite sides of the side branch structure

60. In some embodiments, the first portion 62 of the first full serpentine band 23a and the first portion 62 of the second full serpentine band 23b are oriented on opposite ends of the side branch structure 60. In some embodiments, the first full serpentine band 23a comprises a mirror image of the second full serpentine band 23b taken across the side branch minor axis 78 (see e.g. FIG. 4A).

In some embodiments, a first full serpentine band 23a can be located proximal to the side branch structure 60. In some embodiments, each proximal peak 24 of the first full serpentine band 23a is aligned around a common circumference of the stent. In some embodiments, each distal valley 26 of the first portion 62 is aligned around a common circumference of the stent. In some embodiments, each distal valley 26 of the second portion 63 is aligned around a common circumference of the stent. In some embodiments, the distal valleys 26 of the first and second portions 62, 63 of the first full serpentine band 23a are offset from one another along the length of the stent.

In some embodiments, a second full serpentine band 23b can be located distal to the side branch structure 60. In some embodiments, each distal valley 26 of the second full serpentine band 23b is aligned around a common circumference of the stent. In some embodiments, each proximal peak 24 of the first portion 62 is aligned around a common circumference of the stent. In some embodiments, each proximal peak 24 of the second portion 63 is aligned around a common circumference of the stent. In some embodiments, the proximal peaks 24 of the first and second portions 62, 63 of the second full serpentine band 23b are offset from one another along the length of the stent.

In some embodiments, the first full serpentine band 23a is immediately adjacent to a partial serpentine band 21, and the second full serpentine band 23b is immediately adjacent to another partial serpentine band 21.

In some embodiments, a side branch outer connector 66 connects between the side branch structure 60 and a full serpentine band 23. In some embodiments, a side branch outer connector 66 connects between the side branch structure 60 and a turn 28 of the first portion 62 of the full serpentine band 23. In some embodiments, a side branch outer connector 66 can connect to a proximal peak 24 of the first portion 62 of the full serpentine band 23. In some embodiments, a side branch outer connector 66 can connect to a distal valley 26 of the first portion 62 of the full serpentine band 23.

This structural arrangements shown in FIGS. 2-6 each allow for greater flexibility in the expansion characteristics of the side branch structure 60. The support members 37, 39 are allowed to displace in a stent circumferential direction to a greater extent than in prior art designs during stent expansion. The side branch structure 60 is allowed to displace in circumferential and longitudinal directions to a greater extent than in prior art designs during stent expansion and/or side branch deployment. This in turn allows for greater flexibility in the initial placement of the stent, as a greater range of initial longitudinal and rotational orientations are available, while still providing proper support to a vessel bifurcation.

The inventive stents may be made from any suitable biocompatible materials including one or more polymers, one or more metals or combinations of polymer(s) and metal(s). Examples of suitable materials include biodegradable materials that are also biocompatible. In some embodiments, a stent can have one or more components constructed from one or more metals, polymers or combinations thereof that are corrodible so as to dissolve, dissociate or otherwise break down in the body without ill effect. Examples of such materials have been referred to as being degradable, biodegradable, biologically degradable, erodable, bioabsorbable, bioresorbable, and the like. Biodegradable material will generally undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. Some further examples of biodegradable alloys, such as magnesium alloys and zinc alloys, are disclosed in U.S. Pat. No. 6,854,172 and US 2006/0052864, the entire contents of which are hereby incorporated herein by reference.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent having a central lumen extending between proximal and distal ends of the stent, a circumference circumscribing the central lumen, the stent comprising:
    a side branch structure defining an inner side branch cell, the inner side branch cell having a shape different from any other cell of the stent;
    a first support member and a second support member positioned on opposite sides of the side branch structure, said opposite sides located across the side branch structure from one another in a stent circumferential direction along said circumference, the first support member and the second support member each comprising a strut width that is greater than the width of a strut included in the side branch structure; and
    a first connecting member positioned at a proximal end of the side branch structure and a second connecting member positioned at a distal end of the side branch structure, each connecting member connected at one end to the first support member and connected at the other end to the second support member, each connecting member comprising a serpentine structure having a plurality of first struts, a plurality of second struts, and a plurality of turns connecting ends of the first struts to ends of the second struts, wherein the first struts are straight struts and the second struts have a first straight portion at a first end of the second strut, a second straight portion at a second end of the second strut, and a jog portion with a single u-shaped member connecting the first straight portion to the second straight portion.

2. The stent of claim 1, wherein each connecting member comprises at least two first struts, six second struts, and nine turns.

3. The stent of claim 1, wherein each connecting member defines a plurality of ancillary petals, each ancillary petal comprising at least two second struts located adjacent one another, wherein a longitudinal axis of an ancillary petal passes through a side branch center point.

4. The stent of claim 1, further comprising a plurality of joining members, each joining member connected at one end to a support member and connected at the other end to a different location of the same support member.

5. The stent of claim 1, wherein the side branch structure comprises a serpentine ring having a plurality of straight struts, and wherein each connecting member comprises a strut that is longer than any strut included in the serpentine ring.

6. The stent of claim 5, wherein the serpentine ring comprises struts having the same width as struts of a connecting member.

7. The stent of claim 1, wherein the first support member comprises a mirror image of the second support member, the mirror image taken across a stent longitudinal axis that passes through a center point of the inner side branch cell.

8. The stent of claim 1, wherein the first connecting member comprises a mirror image of the second connecting member, the mirror image taken across a stent circumferential axis that passes through a center point of the inner side branch cell.

9. The stent of claim 1, wherein each stent element extending between the first support member and the second support member comprises a straight portion that is oriented in a non-circumferential direction.

10. The stent of claim 1, wherein the first support member and the second support member each comprise a proximal portion and a distal portion, said proximal portions located at said proximal end of the side branch structure and said distal portions located at said distal end of the side branch structure, each support member comprising a constant width extending between said proximal portion and said distal portion.

11. The stent of claim 1, further comprising a plurality of partial serpentine bands, each partial serpentine band attached at one end to the first support member and attached at the other end to the second support member.

12. The stent of claim 1, wherein the stent does not include any straight struts that connect directly between the first support member and the second support member.

13. The stent of claim 1, the first support member and the second support member each comprising a proximal portion and a distal portion, said proximal portions located at said proximal end of the side branch structure and said distal portions located at said distal end of the side branch structure, wherein a distance between said proximal portions of said support members as measured in a stent circumferential direction increases upon expansion of the stent.

14. The stent of claim 13, wherein a distance between said distal portions of said support members as measured in a stent circumferential direction increases upon expansion of the stent.

15. The stent of claim 1, wherein the first end of said second strut is attached to a first end of said first strut by a first turn, and the second end of said second strut is attached to the second end of an adjacent second strut by a second turn, wherein the jog portion of said second strut confronts the jog portion of the adjacent second strut.

16. A stent having a central lumen extending between proximal and distal ends of the stent, a circumference circumscribing the central lumen, the stent comprising:
    a side branch structure defining an inner side branch cell, the inner side branch cell having a shape different from any other cell of the stent;
    a first support member and a second support member positioned on opposite sides of the side branch structure, said opposite sides located across the side branch structure from one another in a stent circumferential direction along said circumference, the first support member and the second support member each comprising a strut width that is greater than the width of a strut included in the side branch structure; and a first connecting member positioned at a proximal end of the side branch structure and a second connecting member positioned at a distal end of the side branch structure, each connecting member connected at one end to the first support member and connected at the other end to the second support member, each connecting member comprising a serpentine structure having a plurality of struts and turns, including at least one straight strut wherein a length of the strut is at least ten times its width and at least one second strut having a first straight portion at a first end of the second strut, a second straight portion at a second end of the second strut, and a portion with a single u-shaped jog connecting the first straight portion to the second straight portion, wherein said second strut is connected by said turn to said straight strut;

wherein the stent does not include any straight struts that connect directly between the first support member and the second support member.

17. A stent having a length and a central lumen spanning between a proximal end and a distal end, and a circumference circumscribing the central lumen, the stent comprising:

a side branch structure defining an inner side branch cell, the inner side branch cell having a shape different from any other cell of the stent, the side branch structure comprising a serpentine ring extending around the inner side branch cell, the side branch structure spanning a portion of said length;

a first support member and a second support member positioned on opposite sides of the side branch structure, said opposite sides located across the side branch structure from one another in a stent circumferential direction, wherein said stent circumferential direction is a direction along said circumference circumscribing the central lumen, the first support member and the second support member each spanning said portion of said length occupied by the side branch structure, the first support member and the second support member each comprising a strut width that is greater than the width of a strut included in the side branch structure; and a first connecting member positioned at a proximal end of the side branch structure and a second connecting member positioned at a distal end of the side branch structure, each connecting member connected at one end to the first support member and connected at the other end to the second support member, each connecting member comprising a serpentine structure having a plurality of first struts, a plurality of second struts, and a plurality of turns connecting ends of the first struts to ends of the second struts, wherein the first struts are straight struts and the second struts have a first straight portion at a first end of the second strut, a second straight portion at a second end of the second strut, and a jog portion with a single u-shaped member connecting the first straight portion to the second straight portion.

18. The stent of claim 17, further comprising a plurality of partial serpentine bands, each partial serpentine band attached at one end to the first support member and attached at the other end to the second support member.

19. The stent of claim 17, wherein the portion of said first and second support members that span said portion of said length occupied by the side branch structure each comprise a constant width.

20. The stent of claim 17, wherein the stent does not include any straight struts that connect directly between the first support member and the second support member.

* * * * *